United States Patent [19]

Horton et al.

[11] Patent Number: 4,562,177
[45] Date of Patent: Dec. 31, 1985

[54] 3'-AMINO-2' HALO-ANTHRACYCLINE ANTIBIOTICS

[75] Inventors: Derek Horton; Waldemar A. Priebe, both of Columbus, Ohio

[73] Assignee: The Ohio State University Research Foundation, Columbus, Ohio

[21] Appl. No.: 487,841

[22] Filed: Apr. 22, 1983

Related U.S. Application Data

[63] Continuation-in-part of Ser. No. 408,942, Aug. 19, 1982, Pat. No. 4,427,664, which is a continuation of Ser. No. 268,623, May 29, 1981, abandoned.

[51] Int. Cl.[4] .......................... A61K 31/71; C07H 15/24
[52] U.S. Cl. .......................................... 514/34; 536/6.4; 536/122
[58] Field of Search ................. 536/6.4, 122; 424/180; 514/34

[56] References Cited

U.S. PATENT DOCUMENTS

| | | | |
|---|---|---|---|
| 3,590,028 | 6/1971 | Arcamone et al. | 260/210 |
| 3,803,124 | 4/1974 | Arcamone et al. | 260/210 AB |
| 4,046,878 | 9/1977 | Patelli et al. | 424/180 |
| 4,058,519 | 11/1977 | Arcamone et al. | 424/180 |
| 4,067,968 | 1/1978 | Lazzari et al. | 424/180 |
| 4,067,969 | 1/1978 | Penco et al. | 424/180 |
| 4,201,773 | 5/1980 | Horton et al. | 424/180 |
| 4,345,070 | 8/1980 | Suarato et al. | 536/6.4 |

FOREIGN PATENT DOCUMENTS 2519157 11/1975 Fed. Rep. of Germany ....... 536/6.4

OTHER PUBLICATIONS

Fuchs, Ernst–F et al., Carbohydrate Research, 57:C36–C39, (1977).
Cheung, Tak Ming et al., Carbohydrate Research, 58:139–151, (1977).
Horton, Derek et al., Carbohydrate Research, 77:C8–C11, (1977).

Primary Examiner—Johnnie R. Brown
Assistant Examiner—Elli Peselev
Attorney, Agent, or Firm—Sidney W. Millard

[57] ABSTRACT

Compounds of the formula

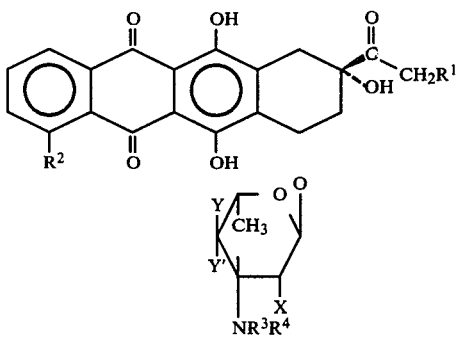

wherein $R^1$ is a hydrogen atom or a hydroxyl group; $R^2$ is a hydrogen atom or a hydroxyl or methoxyl group; X is a fluorine, chlorine, bromine or iodine atom; one of Y and Y' is a hydrogen atom and the other is a hydrogen atom or a hydroxyl or acyloxy group; $R^3$ and $R^4$ are each independently a hydrogen atom, an alkyl group, a halo- or phenyl-substituted alkyl group, an acyl group or a halo- or phenyl-substituted acyl group or $R^3$ and $R^4$ together form a polymethylene chain having 4 to 6 carbon atoms, are useful as anti-tumor agents, especially for treating leukemia; in particular these compounds exhibit high antileukemic activity against P388 murine leukemia.

19 Claims, No Drawings

3'-AMINO-2' HALO-ANTHRACYCLINE ANTIBIOTICS

The invention described herein was made in the course of work under a grant or award from the U.S. Department of health and Human Services.

CROSS-REFERENCE TO RELATED APPLICATIONS

This application is a continuation-in-part of U.S. application Ser. No. 408,942 filed Aug. 19, 1982 (now U.S. Pat. No. 4,427,664) which in turn is a continuation of Ser. No. 268,623 filed May 29, 1981 (now abandoned).

BACKGROUND OF THE INVENTION

This invention relates to 3'-amino-2'halo-anthracycline anti-cancer antibiotics. The term antibiotic is used herein in its original sense to mean "a metabolic product of a microorganism or a derivative thereof" and does not necessarily imply that the compounds possess significant antibacterial activity.

Anthracyline antibiotics including doxorubicin, daunorubicin, and carminomycin have emerged as important chemotherapeutic agents in the treatment of a broad specturm of neoplastic conditions including acute myloblastic and lymphoplastic leukemias. Doxorubicin (also known as Adriamycin) is the subject of U.S. Pat. No. 3,590,028 and is a prescribed antineoplastic agent used in a number of chemotherapeutic treatments.

Certain undesirable side effects have limited the usefulness of know anthracyline antibiotics. One of their more serious side effects, however, is their cardiotoxicity which severly restricts the dosages and the frequency with which the antibiotic can be administered and, in turn, limits their overall effectiveness as anantibiotic. Many of the other side effects which accompany the administration of these agents can be managed by administering other pharmaceutical agents in combination with them; however, the cardiopathic effects are not easily controlled or reversed.

In view of the proven effectiveness of known anthracyclines in the treatment of cancer, efforts have been undertaken to develop less toxic derivatives which can be administered in high, more effective dosages with greater frequency. This invention seeks to provide such derivatives.

SUMMARY OF THE INVENTION

The present invention provides compounds of the formula

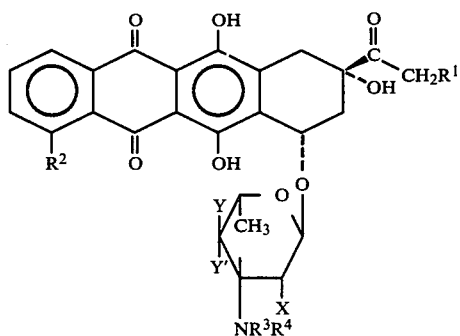

wherein $R^1$ is a hydrogen atom or a hydroxy group; $R^2$ is a hydrogen atom or a hydroxyl or methoxy group; X is a fluorine, chlorine, bromine or iodine atom; one of Y and Y' is a hydrogen atom and the other is a hydrogen atom or a hydroxyl or acyloxy group; $R^3$ and $R^4$ are each independently a hydrogen atom, an alkyl group, a halo-or phenyl-substituted alkyl group, an acyl group or a halo- or phenyl-substituted acyl group, or $R^3$ and $R^4$ together form polymethylene chain having 2 to 6 carbon atoms, and pharmaceutically acceptable acid addition salts thereof.

The present invention also provides pharmaceutical preparations containing the aforesaid compounds in suitable carriers and in therapeutically effective amounts.

The present invention also provides a process for preparing a compound of Formula I above; which comprises treating a compound of the formula

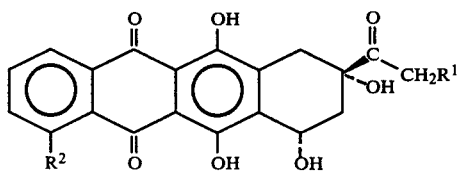

wherein $R^1$ and $R^2$ are as defined above, with a sugar of the formula

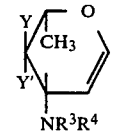

wherein $R^3$, $R^4$, Y or Y' are as defined above except that Y and Y' cannot be a hydroxyl group and $NR_3R_4$ cannot be a free amino group, and with a halogenating and coupling agent in an aprotic solvent.

Finally, the present invention provides a process for treating murine P388 or L1210 leukemia in a test animal, which comprises administering to the test animal a therapeutically-effective amount of a compound of the invention.

DETAILED DESCRIPTION OF THE INVENTION

The instant compounds are 2'-halo-sugar derivatives of the antibiotics doxorubicin, 4-demethoxydoxorubicin, carminomycinone, daunomycinone and 4-demethoxydaunomycinone, and closely related compounds. The instant compounds are derived from these parent compounds (which may hereinafter be referred to as "aglycons") or O-7 coupling of the aglycon with a 2-halo pentose or hexose sugar with a pyranose ring structure. It is believed that similar compounds having furanose rings can similarly be prepared but will have lower activity.

In the instant compounds, $R^1$ is preferably a hydrogen atom, or $R^1$ is a hydroxyl group and $R^2$ is a hydrogen atom or a methoxyl group. Preferably, $R^3$ and $R^4$ are each independently a hydrogen atom, an alkyl group containing not more than about 4 carbon atoms, an acetoxyl group, a trifluoroacetoxyl group or a benzyl group. The compounds in which both $R^3$ and $R^4$ represent hydrogen are particularly preferred. The preferred halogen substituent is iodine, but bromine, chlorine and fluorine substituents may also be used.

In the instant compounds, preferably Y is a hydrogen atom and Y' is an acetoxyl or hydroxyl group.

The term "pharmaceutically acceptable acid addition salts" is used herein to refer to salts which have sufficiently low toxicity that they can be administered to the test animals to be treated in therapeutically effective doses without causing substantial toxic effects to said animals. The preferred acid addition salts are the hydrochlorides, but numerous other acid addition salts may be used, for example the hydrobromides, phosphates and others.

Several particular preferred groups of compounds falling within Formula I are as follows (the 4'-substituent is preferably in the Y' position since this is the configuration in the aforementioned natural antibiotics):

a. The compounds in which X is an iodine atom, Y is a hydrogen atom, Y' is an acetoxyl or hydroxyl group and $R^1$ and $R^2$ are as follows:

$R^1$ is a hydrogen atom and $R^2$ is a methoxy group;
$R^1$ is a hydroxyl group and $R^2$ is a methoxyl group;
$R^1$ is a hydrogen atom and $R^2$ is also a hydrogen atom;
$R^1$ is a hydrogen atom and $R^2$ is a hydroxyl group; or
$R^1$ is a hydroxyl group and $R^2$ is a hydrogen atom b. The compounds in which X is a bromine or iodine atom, one of Y and Y' is a hydrogen atom and the other is an acetoxyl and hydroxyl group, and $R^3$ and $R^4$ are each independently a hydrogen atom or an alkyl group containing not more than about 4 carbon atoms, and especially such compounds in which $R^2$ is a hydrogen atom or a methoxyl group and X is an iodine atom;

c. The compounds in which $R^1$ is a hydrogen atom, $R^2$ is a methoxyl group, $R^3$ is a hydrogen atom, $R^4$ is a trifluoroacetoxyl group, X is an iodine atom, Y is a hydrogen atom and Y' is an acetoxyl group, namely 7-0-(4-0-acetyl-2,3,6-trideoxy-3-trifluoroacetoamido-2-iodo-alpha-L-talo-hexopyranosyl) daunomycinone, and pharmaceutically acceptable acid addition salts thereof.

The sugar moiety in the instant compounds is preferably an alpha-L manno- or alpha L-talo-hexopyranose, (other isomes can also be used) since these sugar residues are particularly effective sustaining or potentiating the pharmaceutical activity of the aglycon moiety. One specific preferred sugar residue is the residue from 4-0 acetyl-15-anhydro-2,3,6-trideoxy-3-trifluoroacetamido-L-lyxo-hex-1-enitol Methods suitable for preparing this and similar 3-amino sugars for use in the instant process are described in, for example, K. Tasuta and T. Takeuchi, J. Antibiotics, 33 (12), 1581 (1980); F. Arcamone and G. Cassinelli, U.S. Pat. No. 4,020,270 (Apr. 26, 1977). As already mentioned, the instant compounds are prepared by reacting the appropriate aglycon with the appropriate unsaturated sugar and a halogenating agent in a aprotic solvent, the sugar, if one carrying a 4-hydroxy group and/or 3-free amino group, being used in a protected form in which these groups are blocked. Naturally, if it is desired to prepare a compound of Formula I in which Y or Y' is a hydroxyl group and/or $R^3$ and $R^4$ are hydrogen, the 4'-acyloxy and/or 3-free amino compound of Formula I prepared by the coupling/halogenation reaction may thereafter be hydrolyzed (by any one of a variety of conventional methods which will be apparent to those skilled in the art) to produce the corresponding 4'-hydroxy compound of Formula I.

As already mentioned, this invention extends to therapeutic compositions containing the instant compounds. As will be apparent to those skilled in the art, such therapeutic compositions may be prepared by dispersing or dissolving the instant compounds in any pharmaceutically acceptable non-toxic carrier suitable for the desired mode of administration. The instant therapeutic compositions are preferably administered parenterally, for example by intravenous, intramuscular, intraperitoneal or other conventional injection. The instant therapeutic compounds may also be administered orally in some cases. For parenteral administration, the compound is desirably administered in an aqueous medium buffered to pH 7.2–7.5, the physiological range; obviously, it is desirable that the aqueous solution be made isotonic, To achieve the necessary pH, any conventional buffer, such as Tris, phosphate, bicarbonate or citrate buffer can be used, as can saline solution.

Preferred halogenating and coupling agents for use in preparing the compounds of Formula I are N-bromo-or N-iodosuccinimide, while a preferred aprotic solvent is an anhydrous mixture of acetonitrile and tetrahydrofuran. The product can be purified by chromatography, a preferred chromatography system being silica gel as the solid phase and a mixture of toluene and acetone as the liquid phase. Further purification of the product may be effected by recrystallization from a mixture of acetone and hexane. The instant compound displays significant activity against murine P388. and L1210 leukemias in test animals and have lower toxicity than the aglycons from which they are derived. The instant compounds are thus useful for treating these leukemias in test animals. In general, the 4-hydroxy-3-free amino compounds are preferred for use because of solubility considerations; the compounds having such groups blocked are of course useful as intermediates in preparing the unblocked compounds.

The synthesis of the compounds of the present invention is illustrated by the following non-limiting example:

Synthesis Example

Synthesis of 7-0-(4-0-acetyl-2,3,6-trideoxy-3-trifluoroacetamido-2-iodo-alpha-L-talo-hexopyranosyl)-daunomycinone.

4-0-Acetyl-1,5-anhydro-2,3,6-trideoxy-3-trifluoroacetamido-L-lyxo-hex-1-enitol (172 mg., 0.644 mmol) was dissolved in acetonitrile (6 mL) and added to a solution of daunomycinone (256.4 mg, 0.644 mmol) in tetrahydrofuran (6 mL). The mixture was flushed with argon and cooled in an ice-bath, and N-iodosuccinimide (217 mg. 0.964 mmol) was added with vigorous stirring. The ice-bath was removed after 10 min and stirring was continued for an additional 24 hours at room temperature. Then the mixture was diluted with dichloromethane (30 ml) and the resultant solution was shaken twice with 10% aqueous sodium thiosulfate (15 ml), washed with water (twice, 20 ml), and dried with magnesium sulfate. Filtration and evaporation of the filtrate gave red oil that was chromatographed on silica gel with 8:1 toluene—acetone. Isolation of the appropriate fraction and crystallization from acetone—hexane gave 82 mg of 7-0-(4-0-acetyl-2,3,6-trideoxy-3-trifluoroacetamido-2-iodo-alpha-L-talo-hexopyranosyl)daunomycinone; m.p. 251°–217°, $[alpha]_D^{23}+84°$ (c,0.02, chloroform); $nu_{max}^{KBr}$ 3450 (bs, OH, NH), 1745 (0-acetyl), 1725 (bs, amide, C-acetyl), 1616 and 1578 cm-1 (chelated quinone), $^1$H-n.m.r. (CDCl$_3$, 200 MHZ); 14.05, 13.28 (s, 1H, HO-6, HO-11), 8.06 (dd, 1H, $J_{1,2}$7.6, $J_{1,3}$0.9 Hz, H-1), 7.80 (apparent t, 1H, H-2), 7.40 (dd, 1H, $J_{2,3}$ 8.5 Hz, H-3), 6.79 (bd, 1H, $J_{NH,3}$, 7.7 Hz, NH), 5.93 (s, 1H H-1'), 5.28 (m, 1H, H-7), 5.15 (m, 1H H-4), 4.45 (m, 2H, H-2', H-3'), 4.10 (s, 3H, OCH$_3$), 4.03 (dq, 1H, H-5'), 3.84 (s, 1H, HO-9), 3.25 (dd, 1H, $J_{8e,10e}$ 1.5 Hz, H-10e), 2.95 (d, 1H, $J_{10ax,10e}$ 18.9 Hz, H-10ax), 2.41 (s, 3H, H-14), 2.31 (m, 1H, H-8e), 2.23 (s, 3H, OAc), 2.17 (m, 1H, H-8ax), 1.25 (d, 3H, $J_{5',6'}$ 6.5 Hz, H-6').

The corresponding carminomycin, doxorubicin, and 4-demethoxydaunomycin compounds can be prepared in an analogous manner using the appropriate aglycon.

It will be apparent to those skilled in the art that numerous changes and modifications can be made in the preferred embodiments of the invention described above without departing from the scope of the invention. For example the groups R$^3$ and R$^4$ could bear substituents other than those described above. Accordingly, the foregoing description is to be construed in an illustrative and not in a limitative sense, the scope of the invention being defined solely by the appended claims.

We claim:

1. A compound of the formula

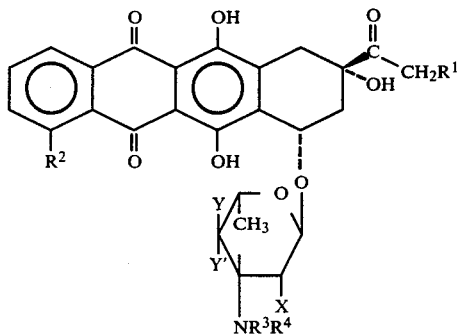

wherein R$^1$ is a hydrogen atom or a hydroxyl group; R$^2$ is a hydrogen atom or a hydroxyl or methoxyl group; X is a fluorine, chlorine, bromine or iodine atom; one of Y and Y' is a hydrogen atom and the other is a hydrogen atom or a hydroxyl or acetoxyl group; R$^3$ and R$^4$ are each independently a hydrogen atom, an alkyl group containing not more than about four carbon atoms, or an acetoxyl, trifluoroacetoxyl or benzyl group, or R$^3$ and R$^4$ together form a polymethylene chain having from 2 to 6 carbon atoms; or a pharmaceutically acceptable acid addition salt thereof.

2. A compound according to claim 1 wherein R$^1$ is a hydrogen atom.

3. A compound according to claim 1 wherein R$^1$ is a hydroxyl group and R$^2$ is a hydrogen atom or a methoxyl group.

4. A compound according to claim 1 wherein R$^3$ and R$^4$ are each independently a hydrogen atom, a alkyl group containing not more than about four carbon atoms, an acetoxyl group, a trifluoroacetoxyl group or a benzyl group.

5. A compound according to claim 4 wherein R$^3$ and R$^4$ are each a hydrogen atom.

6. A compound according to claim 1 wherein X is an iodine atom.

7. A compound according to claim 1 wherein Y is a hydrogen atom and Y' is an acetoxyl or hydroxyl group.

8. A compound according to claim 1 in the form of a hydrochloride salt.

9. A compound according to claim 1 wherein Y' is an acetoxyl or hydroxyl; X is an iodine atom; and R$^1$ and R$^2$ are selected as follows:

R$^1$ is a hydrogen atom and R$^2$ is a methoxy group;
R$^1$ is a hydroxyl group and R$^2$ is a methoxyl group;
R$^1$ is a hydrogen atom and R$^2$ is also a hydrogen atom;
R$^1$ is a hydrogen atom and R$^2$ is a hydroxyl group; or
R$^1$ is a hydroxyl group and R$^2$ is a hydrogen atom.

10. A compound according to claim 1, wherein R$^1$ is hydrogen, or R$^1$ is a hydroxyl group and R$^2$ is a methoxyl group; R$^3$ and R$^4$ are both hydrogen atoms; and one of Y and Y' is a hydrogen atom and the other is a hydroxyl or acetoxyl group.

11. A compound according to claim 1 wherein X is a bromine or iodine atom; one of Y and Y' is a hydrogen atom and the other is an acetoxyl or hydroxyl group; and R$^3$ and R$^4$ are each independently a hydrogen atom or an alkyl group containing not more than four carbon atoms.

12. A compound according to claim 11 wherein R$^2$ is a hydrogen atom or a methoxyl group and X is an iodine atom.

13. The compound according to claim 1 wherein R$^1$ is a hydrogen atom, R$^2$ is a methoxyl group, R$^3$ is a hydrogen atom, R$^4$ is a trifluoroacetoxyl group, X is an iodine atom, Y is a hydrogen atom and Y' is a acetoxyl group, namely 7-0-(4-0-acetyl-2,3,6-trideoxy-3-trifluoroacetamido-2-iodo-alpha-L-talo-hexopyranosyl)-daunomycinone, and pharmaceutically acceptable acid addition salts thereof.

14. A compound according to claim 1 having a sugar moiety derived from an alpha-L-manno-or alpha-L-talo-hexopyranose.

15. A compound of the formula

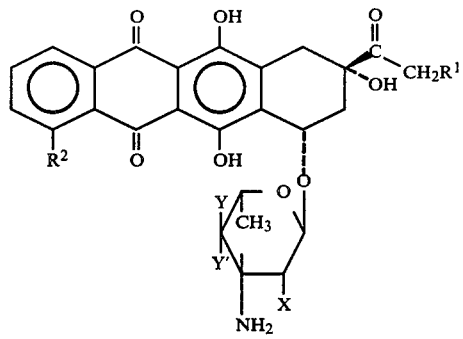

wherein R$^1$ is a hydrogen atom or a hydroxyl group; R$^2$ is a hydrogen atom or a hydroxyl or methoxyl group; X is a fluorine, chlorine, bromine or iodine atom; and one of Y and Y' is a hydrogen atom and the other is a hydrogen atom or a hydroxyl group.

16. A pharmaceutical composition for treatment of murine P388 and L1210 leukemia in test animals, said composition comprising a carrier and a therapeutically effective amount of a compound of the formula

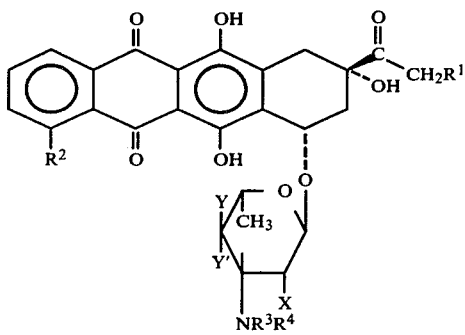
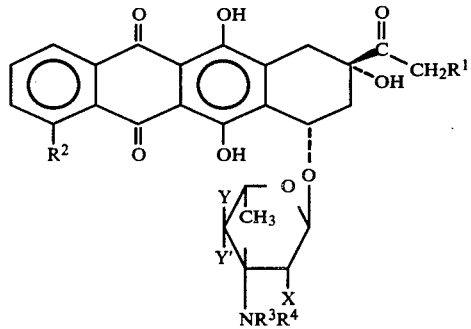

wherein $R^1$ is a hydrogen atom or a hydroxyl group; $R^2$ is a hydrogen atom or a hydroxyl or methoxyl group; X is a fluorine, chlorine, bromine or iodine atom; one of Y and Y' is a hydrogen atom and the other is a hydrogen atom or a hydroxyl or acetoxyl group; $R^3$ and $R^4$ are each independently a hydrogen atom, an alkyl group containing not more than about four carbon atoms, or an acetoxyl, trifluoroacetoxyl or benzyl group, or $R^3$ and $R^4$ together form a polymethylene chain having from 2 to 6 carbon atoms; or a pharmaceutically acceptable acid addition salt thereof.

17. A method for treating murine P388 or L1210 leukemia in a test animal, which method comprises administering to said test animal a therapeutically-effective amount of a compound of the formula wherein $R^1$ is a hydrogen atom or a hydroxyl group; $R^2$ is a hydrogen atom or a hydroxyl or methoxyl group; X is a fluorine, chlorine, bromine or iodine atom; one of Y and Y' is a hydrogen atom and the other is a hydrogen atom or a hydroxyl or acetoxyl group; $R^3$ and $R^4$ are each independently a hydrogen atom, an alkyl group containing not more than about four carbon atoms, or an acetoxyl, trifluoroacetoxyl or benzyl group. or $R^3$ and $R^4$ together form a polymethylene chain having from 2 to 6 carbon atoms; or a pharmaceutically-acceptable acid addition salt thereof.

18. A method according to claim 17 wherein said compound is administered by parenterally or orally.

19. A method according to claim 17 wherein said compound is administered parenterally in the form of an isotonic solution buffered by a pH in the range of about 7.2 to about 7.5.

* * * * *